United States Patent [19]

Anderson

[11] Plant 4,078

[45] July 19, 1977

[54] DWARF NECTARINE TREE

[75] Inventor: Frederic W. Anderson, Merced, Calif.

[73] Assignee: Stribling's Nurseries, Inc., Merced, Calif.

[21] Appl. No.: 717,861

[22] Filed: Aug. 25, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A genetically dwarf nectarine tree which is of comparatively medium size, medium vigor, spreading, dense, foliated with large to medium size, lanceolate leaves having a crenate margin, flowering mid-season with large flowers, and a productive and regular bearer of early ripening, medium size, symmetrical, globose, freestone fruit having yellow skin substantially overspread with red, and yellow flesh.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of dwarf nectarine tree resulted from my endeavors in the conduct of such plant breeding program.

ORIGIN OF THE VARIETY

The present variety of genetically dwarf nectarine tree was originated by me, in my experimental nursery and orchard located as aforesaid, as an open-pollinated dwarf seedling from an unnamed tall or full-size nectarine tree which was selected from the $F_1$ progeny of a cross of Golden Prolific nectarine (U.S. Plant Pat. No. 2,193) as the seed parent, with the May Grand nectarine (U.S. Plant Pat. No. 2,794) as the pollen parent. The variety, as thus originated, and under careful and continuing observation, evidenced — upon bearing fruit — certain novel characteristics which were commercially desirable, and I, therefore, undertook asexual reproduction of the variety preparatory to introducing it to the trade.

ASEXUAL REPRODUCTION OF THE VARIETY

Subsequent to origination and selection by me of the present variety of nectarine tree, in the manner above described, I asexually reproduced it by top-working on mature trees in my said experimental orchard, and — in maturity — such reproductions ran true to the original tree in all respects.

SUMMARY OF THE VARIETY

The herein claimed new and distinct variety of genetically dwarf nectarine tree is of comparatively medium size, medium vigor, spreading, dense, foliated with large to medium size, lanceolate leaves having a crenate margin, flowering mid-season with large flowers, and a productive and regular bearer of early ripening, medium size, symmetrical, globose, freestone fruit having yellow skin substantially overspread with red, and yellow flesh; the variety being characterized by fruit which ripens about 2 weeks earlier than the Golden Prolific nectarine, and which fruit has a red exterior color brighter than said Golden Prolific nectarine and resembling the May Grand nectarine in such respect.

BRIEF DESCRIPTION OF THE DRAWING

The drawing is an illustration, by photographic reproduction in color, of leaves and fruit of the variety; one of the fruit being cut into halves to expose the flesh, with the stone remaining in one such half.

DESCRIPTION OF THE VARIETY

The botanical details of this new and distinct variety of dwarf nectarine tree — with color definitions (except those in common color terms) referenced to Maerz and Paul Dictionary of Color — are as follows:

Tree:
- *Class.*—Genetically dwarf.
- *Size.*—Medium, as compared with other dwarf nectarine trees.
- *Vigor.*—Medium.
- *Growth.*—Spreading.
- *Density.*—Dense.
- *Production.*—Productive.
- *Bearing.*—Regular bearer.

Trunk:
- *Size.*—Medium.

Branches:
- *Size.*—Medium.

Leaves:
- *Size.*—Large to medium; average length — 6¼"; average width — 1".
- *Form.*—Lanceolate.
- *Margin.*—Crenate.
- *Petiole.*—Medium length — average ¾" ; thick.
- *Glands.*—Number and position — usually 2 to 3 on petiole and 2 on blade; alternate; reniform.
- *Color.*—Top side — Medium green (22-L-8); under side — Lighter green (21-L-7).

Flower buds:
- *Size.*—Large.

Flowers:
- *Blooming period.*—mid-season; medium, as compared with other varieties.
- *Size.*—Large.

Fruit:

*Maturity when described.*—Eating ripe — June 25th, 1976.

*Date of first picking.*—June 15th, 1976.

*Date of last picking.*—June 25th, 1976.

*Size.*—Medium; uniform; average diameter axially — $2\frac{1}{8}''$; average transversely in suture plane — $2\frac{3}{8}''$.

*Form.*—Uniform; symmetrical; globose.

*Suture.*—Shallow; an inconspicuous line.

*Ventral Surface.*—Rounded strongly.

*Cavity.*—Circular; average depth — $\frac{1}{4}''$; average breadth — $\frac{3}{8}''$.

*Base.*—Rounded.

*Apex.*—Short; depressed.

Skin:

*Thickness.*—Medium.

*Texture.*—Medium.

*Tendency to crack.*—None noted.

*Down.*—Wanting.

*Color.*—Yellow (9-L-4) substantially overspread with red (6-L-5) shading darker to 7-L-5, with many yellow flecks.

Flesh:

*Juice.*—Abundant; rich.

*Texture.*—Firm; crisp; melting.

*Ripens.*—Evenly.

*Flavor.*—Subacid; delicate.

*Eating quality.*—Good.

*Color.*—Yellow (9-L-5).

*Surface of pit cavity.*—Yellow.

Stone:

*Type.*—Free.

*Size.*—Medium; average length — $1\frac{1}{8}''$; average breadth — $1''$; average thickness — $\frac{5}{8}''$.

*Form.*—Oblong.

*Base.*—Straight.

*Apex.*—Rounded.

*Sides.*—Equal.

*Pits.*—Elongated.

*Ventral edge.*—Thick.

*Dorsal edge.*—Full, with broad groove.

*Tendency to split.*—None noted.

*Color.*—Beige (12-I-7).

Use: Market — local. Dessert. Culinary. Canning.

Keeping quality: Good.

Resistance to insects and diseases: No unusual susceptibilities noted.

Shipping quality: Good.

The dwarf nectarine tree and its fruit herein described may vary in slight detail due to climatic and soil conditions under which the variety may be grown; the present description being of the variety as grown in the Central Valley of California.

I claim:

1. A new and distinct variety of genetically dwarf nectarine tree, substantially as shown and described, which is of comparatively medium size, medium vigor, spreading, dense, foliated with large to medium size, lanceolate leaves having a crenate margin, flowering mid-season with large flowers, and a productive and regular bearer of early ripening, medium size, symmetrical, globose, freestone fruit having yellow skin substantially overspread with red, and yellow flesh; the variety being characterized by fruit which ripens about two weeks earlier than the Golden Prolific nectarine, and which fruit has a red exterior color brighter than said Golden Prolific nectarine and resembling the May Grand nectarine in such respect.

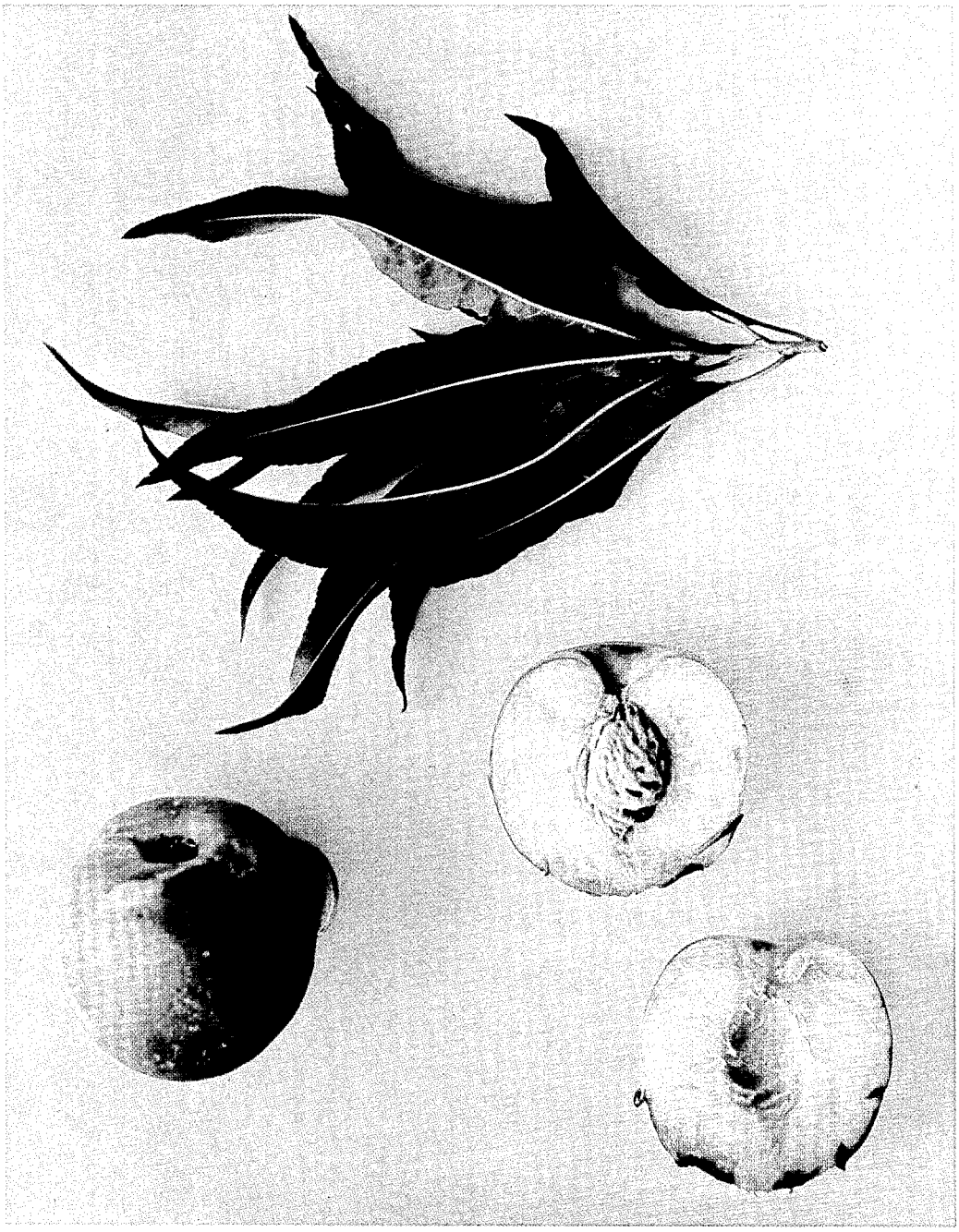

* * * * *